United States Patent
Proksa et al.

(10) Patent No.: US 10,055,859 B2
(45) Date of Patent: Aug. 21, 2018

(54) CT IMAGING APPARATUS WITH SPARSE ANGULAR SAMPLING

(71) Applicant: KONINKLIJKE PHILIPS N.V., Eindhoven (NL)

(72) Inventors: Roland Proksa, Neu Wulmstorf (DE); Michael Grass, Buchholz in der Nordheide (DE); Thomas Koehler, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 35 days.

(21) Appl. No.: 15/317,133

(22) PCT Filed: Jun. 16, 2015

(86) PCT No.: PCT/EP2015/063380
§ 371 (c)(1),
(2) Date: Dec. 8, 2016

(87) PCT Pub. No.: WO2015/197419
PCT Pub. Date: Dec. 30, 2015

(65) Prior Publication Data
US 2017/0124732 A1    May 4, 2017

(30) Foreign Application Priority Data
Jun. 25, 2014 (EP) .................................. 14173805

(51) Int. Cl.
*G06T 11/00* (2006.01)
*A61B 6/03* (2006.01)
*A61B 6/00* (2006.01)

(52) U.S. Cl.
CPC ............ *G06T 11/005* (2013.01); *A61B 6/032* (2013.01); *A61B 6/5205* (2013.01); *G06T 2211/412* (2013.01); *G06T 2211/436* (2013.01)

(58) Field of Classification Search
CPC .... G06T 11/003; G06T 11/005; G06T 11/006; G06T 2211/412; G06T 2211/436;
(Continued)

(56) References Cited

U.S. PATENT DOCUMENTS 5,966,422 A    10/1999  Dafni et al. ....................... 378/9
6,529,574 B1   3/2003   Hsieh ............................... 378/4
(Continued)

FOREIGN PATENT DOCUMENTS

WO    2013/064472 A1    5/2013

OTHER PUBLICATIONS

Giles William et al: "Interleaved acquisition for cross scatter avoidance in dual cone-beam CT", Medical Physics, AIP, Melville, NY, US, vol. 39, No. 12, (Dec. 1, 2012), pp. 7719-7728.
(Continued)

*Primary Examiner* — Andrew W Johns

(57) ABSTRACT

The invention relates to a CT imaging apparatus and a method for generating sectional images of an object such as a patient on a patient table. According to one embodiment, first projections (P) are generated along a first helical scanning path (Tr1) of a first X-ray source according to a sparse angular sampling scheme. Additional projections ($Q_1$, $Q_2$, $R_1$) may dynamically be introduced along said first helical scanning path (Tr1) and/or along a second helical scanning path (Tr2) of an additional X-ray source based on the evaluation of previous projections ($P_1$).

20 Claims, 3 Drawing Sheets

(58) Field of Classification Search
CPC ......... A61B 6/03; A61B 6/032; A61B 6/5205; A61B 6/5294
See application file for complete search history.

(56) References Cited

U.S. PATENT DOCUMENTS

| | | | |
|---|---|---|---|
| 7,639,774 B2 | 12/2009 | De Man et al. | 378/9 |
| 8,320,519 B2 | 11/2012 | Ribbing et al. | 378/9 |
| 2006/0146983 A1* | 7/2006 | Kalke et al. | 378/4 |
| 2013/0070994 A1 | 3/2013 | Liang et al. | G06T 7/0012 |
| 2014/0369458 A1* | 12/2014 | Shen et al. | G01N 23/046 |
| | | | 378/5 |

OTHER PUBLICATIONS

Sidky, et al., "Accurate image reconstruction from few-views and limited-angle data in divergent-beam CT", Journal of X Ray Science and Technology 14 (2006) 119-139.

Lee, at al., "Effects of sparse sampling schemes on image quality in low-dose CT", Med. Phys. 40, 111915 (2013).

* cited by examiner

CT IMAGING APPARATUS WITH SPARSE ANGULAR SAMPLING

CROSS REFERENCE TO RELATED APPLICATIONS

This application is the U.S. National Phase application under 35 U.S.C. § 371 of International Application No. PCT/EP2015/063380, filed Jun. 16, 2015, published as WO 2015/197419 on Dec. 30, 2015, which claims the benefit of European Patent Application Number 14173805.4 filed Jun. 25, 2014. These applications are hereby incorporated by reference herein.

FIELD OF THE INVENTION

The invention relates to a method and a CT imaging apparatus for generating sectional images of an object, for example of a patient.

BACKGROUND OF THE INVENTION

The U.S. 2013/0070994 A1 discloses a Computed Tomography (CT) imaging apparatus that is operating with a sparse angular sampling scheme for generating images of the heart. Projections used for image reconstruction are selected based on electrocardiogram-data in order to avoid artefacts due to heart beat.

Moreover, cone-beam CT using two orthogonal X-ray systems for reducing imaging time and for providing simultaneous orthogonal views in planar imaging has been studied in literature (GILES WILLIAM et al.: "Interleaved acquisition for cross scatter avoidance in dual cone-beam CT", MEDICAL PHYSICS, AIP, MELVILLE, N.Y., US, vol. 39, no. 12, (2012-12-01), pages 7719-7728). The authors of that study propose an interleaved acquisition in order to avoid negative effects of cross scatter.

SUMMARY OF THE INVENTION

Based on this background, it was an object of the present invention to provide means that allow for in improved image reconstruction in CT imaging applications with a sparse angular sampling of projections.

This object is achieved by the CT imaging apparatus according to claim 1 and a method according to claim 2. Preferred embodiments are disclosed in the dependent claims.

According to a first aspect, an embodiment of the invention relates to a CT (Computed Tomography) imaging apparatus for generating sectional images of an object, for example of the body of a patient lying on a patient table. The imaging apparatus comprises the following components:

At least one X-ray source for controllably emitting an X-ray beam towards the object (or, more generally, towards a space where the object is typically accommodated).

An X-ray detector for generating projections from said X-ray beam (after its passage through the object).

A control unit for controlling the activity of the X-ray source such that a) first projections are generated according to a sparse angular sampling scheme;

b) additional projections are generated additionally to the first projections of the sparse angular sampling scheme.

A reconstruction unit for reconstructing a sectional image of the object from the first projections and the additional projections.

As known in the art, Computed Tomography is a technique for reconstructing sectional images of an object from projections of the object taken from a sufficient number of different viewing angles. Analytical reconstruction methods require dense angular sampling over an interval of at least 180° to generate good images. A rule of thumb is to measure at least 1.5 projections per image voxel in one dimension (e.g. a 512×512 image matrix requires at least 768 projections). Apart from this, it is also known to use a "sparse angular sampling scheme" in which the X-ray source is repeatedly switched on and off in order to generate projections only from a small number of viewing angles, thus reducing the X-ray exposure of the patient. Algorithms such as "sparse data reconstruction" are needed in this case to deal with the limited number of projection views. Most sparse data reconstruction methods are based on iterative reconstruction algorithms. They can produce high quality CT images from as few as 20 angular views. An example of a sparse data reconstruction technique is described in "Accurate image reconstruction from few-views and limited-angle data in divergent-beam CT" (Emil Y. Sidky, Chien-Min Kao and Xiaochuan Pan, Journal of X-Ray Science and Technology 14 (2006) 119-139). In embodiments of the present invention, "sparse angular sampling" typically means that there are less than about one projection, less than about 0.5 projections, or preferably less than about 0.15 projections per image voxel in one dimension.

The angle that is referred to in the term "angular" is typically measured with respect to a radius originating on the central axis of the CT apparatus and lying in a plane perpendicular to this axis, wherein X-ray emission and detection typically rotate about said axis.

The X-ray source may be any source that can be controlled to emit X-ray beams at the desired angular positions only. It may for example be a conventional X-ray tube, a carbon-nanotube-based tube or the like.

The X-ray beam generated by the X-ray source will typically be fan-shaped or cone-shaped depending on the individual design of the imaging apparatus and the associated X-ray detector.

The X-ray detector may be any kind of detector that is sensitive for X-rays and that allows for a spatially resolved determination of X-ray intensity in a given detector area. It may particularly comprise solid-state detectors with a direct or indirect conversion of incident X-rays into electrical signals in a (one- or two-dimensional) array of pixels.

The control unit and the reconstruction unit may be realized by dedicated electronic hardware, digital data processing hardware with associated software, or a mixture of both. Moreover, the control unit and the reconstruction unit may be combined in a single device.

The first projections that are generated according to a sparse angular sampling scheme are by definition sufficient for the reconstruction of the sectional image of the object. Apart from this minimal set of projections, "additional projections" are generated and used in the reconstruction procedure of the sectional image. The information comprised by these additional projections can favorably be used to improve the accuracy of the resulting reconstructed image.

According to a second aspect, an embodiment of the invention relates to a method for generating sectional images of an object, said method comprising the following steps:

Generating first projections of the object according to a sparse angular sampling scheme.

Generating additional projections of the object additionally to those of the sparse angular sampling scheme.

Reconstructing a sectional image of the object from the first projections and the additional projections.

The imaging apparatus and the method described above are based on the same concept, i.e. the augmentation of a set of first projections by additional projections. Explanations and embodiments described for the imaging apparatus are therefore analogously valid for the method and vice versa.

In the following, various preferred embodiments of the imaging apparatus and the method will be described in more detail.

In a first preferred embodiment, the imaging apparatus comprises a first X-ray source and (at least) one additional X-ray source, wherein the latter is controlled by the control unit to generate the additional projections (i.e. to generate X-ray beams from which the X-ray detector generates said additional projections). Different allocations between first and additional projections on the one hand side and first and additional X-ray source on the other hand side are preferred:

The first X-ray source may generate only first projections and the additional X-ray source may generate only additional projections.

The first X-ray source may generate only first projections and the additional X-ray source may generate additional projections and first projections.

The first X-ray source may generate first projections and additional projections and the additional X-ray source may generate only additional projections.

If first projections are generated by both the first and the additional X-ray source, any suitable allocation of the whole set of first projections to the two sources is possible, in particular regular (i.e. non-random) allocations such as a temporally alternating activity of first and additional X-ray source for the generation of first projections.

Similarly, if additional projections are generated by both the first and the additional X-ray source, any suitable allocation of the whole set of additional projections to the two sources is possible, in particular regular allocations such as a temporally alternating activity of first and additional X-ray source for the generation of additional projections.

CT imaging apparatuses with more than one X-ray source are known in the art (e.g. U.S. Pat. No. 7,639,774). In such an apparatus, a first X-ray source can favorably be used for the generation of the first projections according to a sparse sampling scheme while the additionally available X-ray source(s) can be used for generating additional projections (and optionally also some of the first projections).

There are various possibilities how and where (i.e. from which position of X-ray source and detector) additional projections can be taken. According to one embodiment, (at least) one additional projection is generated in the angular interval between two first projections. Preferably, an additional projection is generated approximately in the middle or center of the angular interval between two first projections (i.e. if two neighboring first projections are generated at angles $\varphi_1$ and $\varphi_2$, respectively, then the additional projection may be generated at an angle of about $(\varphi_1+\varphi_2)/2$). The additional projections will then typically provide the highest possible information in addition to the information conveyed by the regular first projections.

In general, the first projections may be generated with any angular distribution that is in line with an appropriate sparse angular sampling scheme. In a preferred embodiment, first projections are generated at equidistant angular positions.

The angles $\varphi_i$ at which first projections $P_i$ are generated can in this case be expressed by the formula $$\varphi_i = \varphi_0 + i \cdot \Delta\varphi$$

with i=1, 2, 3, ... indexing the projections, $\varphi_0$ being a given starting angle, and $\Delta\varphi$ being a given angular interval between neighboring viewing positions. If this approach is combined with the aforementioned generation of additional projections in the middle between two first projections, the angles $\psi_i$ of the additional projections can be expressed by the following formula:

$$\psi_i = \varphi_0 + (i+0.5) \cdot \Delta\varphi$$

According to another embodiment of the invention, at least one additional projection is dynamically introduced depending on the evaluation of at least one previous projection. In general, the "previous projection" may be a first projection or an additional projection, this does not matter. As its name indicates, the previous projection must however be one that has already been generated prior to the possible introduction/generation of the considered additional projection(s). This embodiment of the imaging apparatus or the method has the advantage that scanning parameters can be adapted dynamically during the scan based on already available projection data. If the latter indicate for example that the first projections alone are not sufficient to achieve a desired accuracy of the sectional image to be reconstructed, additional projections may be introduced into the current scan.

According to a further development of the aforementioned embodiment, at least one additional projection is introduced if the previous projection(s) show(s) an increase in higher spatial frequencies. The "spatial frequencies" of a projection can by definition be determined from the spectrum that is derived from a spatial Fourier analysis of the projection. An "increase in higher spatial frequencies" then means that the spectrum is shifted to higher spatial frequencies with respect to some reference spectrum. This comparison between two spectra may for example be quantified via a comparison of their centers of gravity (i.e. their average frequencies), of the maximal frequencies comprised by the spectra or the like. The reference spectrum with which the previous projection is compared may for example be some spectrum determined in advance, or an average of spectra determined from already accomplished projections (prior to the previous projection).

In another embodiment, the above mentioned at least one previous projection may be generated with another X-ray source than the X-ray source used to generate the associated introduced projection. As explained above, CT imaging apparatuses are known that comprise two or more X-ray sources which can be operated independently and in parallel. The viewing positions assumed by the X-ray source with which the previous projection is generated preferably advance the viewing positions of the X-ray source with which the introduced additional projection is generated during the scanning procedure. In this case the first mentioned X-ray source explores viewing positions or perspectives that are only later encountered by the other X-ray source (the term "viewing position" of an X-ray source shall denote the spatial position of said X-ray source during the generation of a projection).

The at least one additional projection may preferably be introduced at a viewing perspective that corresponds to the viewing perspective of the associated previous projection. In this context, the term "viewing perspective" shall characterize the line of sight of a projection, which is determined by the spatial positions of X-ray source and X-ray detector during the generation of the projection. The previous projection taken at a certain viewing perspective provides information that is related to this perspective, for example the content of spatial frequencies of a projection from this perspective. If this information is used to decide whether an additional projection is introduced or not, it is reasonable to insert this additional projection at a viewing perspective similar to that the decision was based on. If the sectional image to be reconstructed corresponds to a two-dimensional (2D) slice through the object, the X-ray source(s) (and/or the X-ray detector) typically rotates within a plane about a central point to generate projections from positions within this plane. If the sectional image to be reconstructed corresponds to a three-dimensional (3D) image representing a volume of the object, the X-ray source(s) (and/or the X-ray detector) typically rotates on a helical path about a central axis to generate projections from positions on this helical path. Accordingly, the first projections, the additional projections, and/or the above mentioned previous projections may optionally be generated along a helical scanning path.

The reconstruction of the sectional image may in general be done with any appropriate mathematical procedure that can cope with the sampled projections. Most preferably, the reconstruction is done by an iterative procedure (for example as described in Sidky et al., above).

The described methods will typically be realized with the help of a computing device, e.g. a microprocessor or an FPGA in the control unit and/or the reconstruction unit of the imaging apparatus. Accordingly, the present invention further includes a computer program product which provides the functionality of any of the methods according to the present invention when executed on a computing device.

Further, the present invention includes a data carrier, for example a floppy disk, a hard disk, an EPROM, a compact disc (CD-ROM), a digital versatile disc (DVD), or a USB stick which stores the computer product in a machine readable form and which executes at least one of the methods of the invention when the program stored on the data carrier is executed on a computing device. The data carrier may particularly be suited for storing the program of the computing device mentioned in the previous paragraph.

Nowadays, such software is often offered on the Internet or a company Intranet for download, hence the present invention also includes transmitting the computer product according to the present invention over a local or wide area network.

BRIEF DESCRIPTION OF THE DRAWINGS

These and other aspects of the invention will be apparent from and elucidated with reference to the embodiments described hereinafter.

In the drawings.

Like reference numbers refer in the figures to identical or similar components.

DETAILED DESCRIPTION OF EMBODIMENTS

Figure 1:
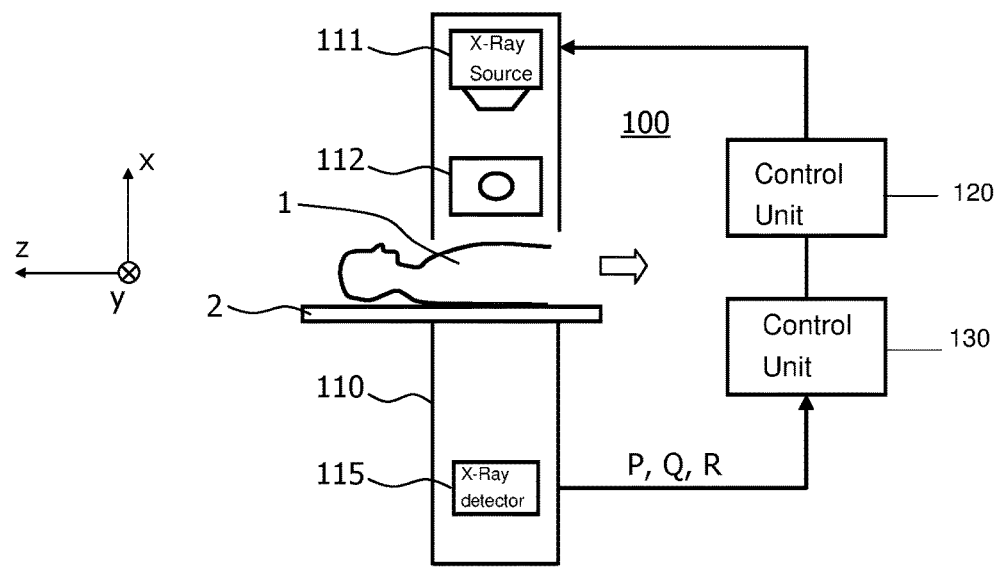
FIG. 1 schematically illustrates a CT imaging apparatus according to an embodiment of the present invention.

FIG. 1 schematically illustrates a CT imaging apparatus 100 according to an embodiment of the present invention. The imaging apparatus 100 comprises a gantry 110 on which a first X-ray source 111 is rotatably mounted opposite to an X-ray detector 115. Moreover, in some embodiments of the invention at least one additional X-ray source 112 may be mounted on the gantry at an angular (and optionally also axially) different position from the first X-ray source, wherein a detector area (not shown) opposite to this additional X-ray source is provided for generating associated projections. This embodiment corresponds to the so-called Stereo tube CT concept. A stereo tube CT scanner has two focal spots (in one or two X-ray tubes) radiating one detector alternatively.

Furthermore, a patient support or table 2 is provided on which a patient 1 to be examined can rest. Typically, the X-ray sources 111, 112 and the detector 115 can commonly rotate in the xy-plane about the central axis (z-axis) of the patient table such that projections of the patient can be generated from different viewing angles. From these projections, a (2D) sectional image of the patient can be reconstructed.

Moreover, the patient table 2 is typically movable in axial direction (z-direction, cf. block arrow). Relative movement between the patient and the X-ray sources/X-ray detector during the scanning procedure will then result in a helical scanning path winding about the patient such that X-ray projections from different viewing angles and different axial positions are generated. From these data, a (3D) sectional image of a body volume can be reconstructed.

The imaging apparatus 100 further comprises a control unit 130 that is coupled to the X-ray sources 111, 112 and preferably also to the X-ray detector 115 for controlling the activity of the X-ray sources, i.e. for timing the generation of associated X-ray beams. Moreover, a reconstruction unit 140 is provided that is coupled to the X-ray detector 115 to receive projections (projection data) P, Q, R from the detector which are stored and processed by said unit. In particular, the reconstruction unit 140 may be adapted to reconstruct sectional images from these projections. The reconstruction unit 140 and the control unit 130 are preferably coupled such that for example information from the reconstruction unit can be forwarded to the control unit. This allows for a dynamic adaptation of the control of the X-ray sources depending on previous projections received by the reconstruction unit.

In the following a novel acquisition technique for sparse angular sampling will be described with respect to the exemplary CT imaging apparatus 100.

Sparse angular sampling is an acquisition technique in which the X-ray flux is rapidly switched on and off during an acquisition to measure a limited number of projections. In combination with advanced reconstruction (iterative) the image quality can be kept close to a full acquisition, while the X-ray dose is reduced. In order to increase the accuracy of image reconstruction and to fully exploit available resources (particularly of a Stereo tube CT apparatus), it is proposed to introduce additional projections supplementary to the "first projections" that are generated according to a sparse angular sampling scheme.

In a first particular embodiment of the aforementioned general approach, it is proposed to interleave the angular samples (projections) of the two X-ray sources. The first X-ray source 111 may for example be switched on for gantry angles $$\varphi_i = \varphi_0 + i \cdot \Delta\varphi$$

with i=1, 2, 3, . . . , $\varphi_0$ and $\Delta\varphi$ being given, while the additional second X-ray source 112 uses angles $$\psi_i \varphi_0 + (i+0.5) \cdot \Delta\varphi.$$

Figure 2:
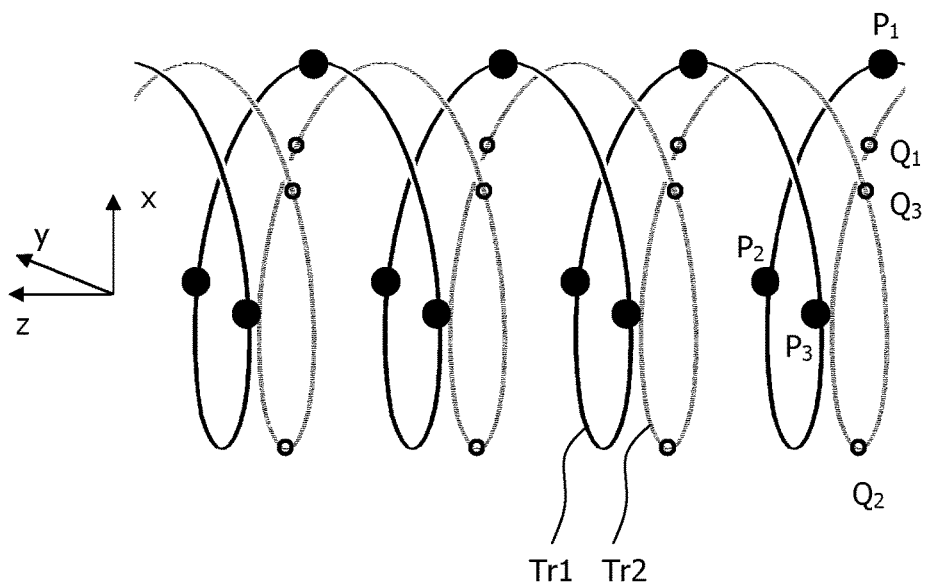
FIG. 2 shows a schematic perspective view of the helical scanning path of a first X-ray source and the helical scanning path of an additional X-ray source when additional projections are introduced between first projections.

FIG. 2 schematically illustrates the helical scanning path Tr1 of the first X-ray source 111 about the axis of the patient. At viewing positions that are distributed in equal angular intervals $\Delta\varphi$ along the helical path, first projections $P_1$, $P_2$, $P_3$, . . . of the object are generated according to a sparse angular sampling scheme by switching the X-ray source 111 on only at these positions (note: the reference signs $P_1$ etc. of the projections are drawn next to the corresponding viewing position of the X-ray source).

Moreover, the helical path Tr2 of the additional X-ray source 112 is shown, which has an axial offset (lag) with respect to the path Tr1 of the first X-ray source 111. By open circles, positions are indicated on this path at which the additional X-ray source 112 is activated to generate additional projections $Q_1$, $Q_2$, $Q_3$ . . . of the object (again, the reference signs $Q_1$ etc. of these projections are drawn next to the corresponding viewing position of the X-ray source).

Figure 3:
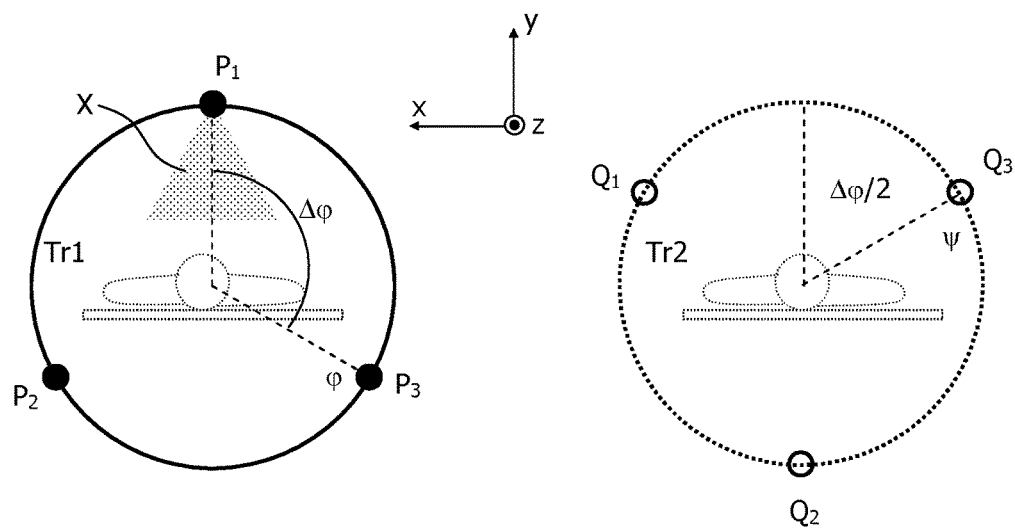
FIG. 3 shows front view of the scanning paths of the first X-ray source (left) and the additional X-ray source (right) of FIG. 2.

According to the above formulae, the additional projections $Q_1$, $Q_2$, $Q_3$ . . . are generated at positions $\psi_i$ just in the middle of the angular internals $\Delta\varphi$ between two first projections. This can best be seen in FIG. 3 from the separate front views onto the first helical path Tr1 (left) and on the second helical path Tr2 (right), respectively.

Figure 4:
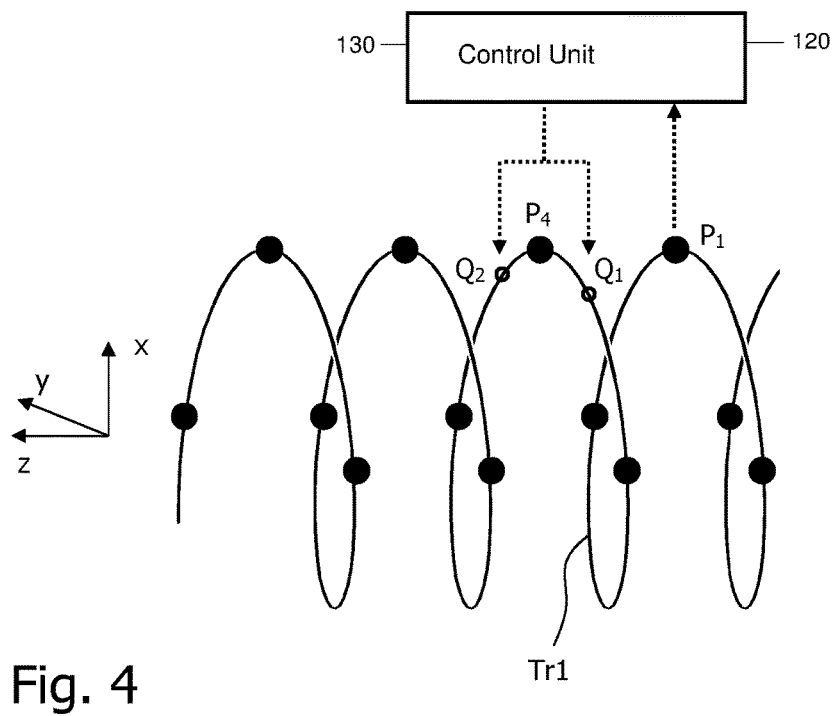
FIG. 4 shows a schematic perspective view of the helical scanning path of a first X-ray source when additional projections are dynamically introduced in said path.

FIG. 4 refers to a second particular embodiment of the above mentioned general approach. The figure shows schematically the helical path of a single (first) X-ray source. This embodiment can therefore also be applied with a conventional CT scanner (without a stereo tube). Again, viewing positions at which the X-ray source is activated to generate first projections $P_1$, . . . according to a sparse angular sampling scheme are indicated by full circles next to the sign of the corresponding projection. In this embodiment, "previous projections" that have already been generated are used and evaluated for deciding if one or more additional projections $Q_1$, $Q_2$, . . . shall be inserted. In the shown situation, the first projection $P_1$ has served as such a "previous projection" based on which it was decided to introduce two additional projections $Q_1$, $Q_2$. As shown, these additional projections are preferably introduced at viewing positions which are close to the viewing position of the previous projection they are based on (in the shown example, the additional projections lie at roughly the same angle $\varphi$ with about one pitch difference in axial direction).

The dynamic introduction of additional projections may for example rely on the following considerations:

The angular subsampling rate at sparse angular sampling must not be too low to avoid sub sampling artifacts. The required sampling frequency typically depends on the spatial frequency of the scanned object. For a given projection angle the important frequency components are orthogonal to the projection angle and are therefore accessible in the projection itself (a proper estimation of the required subsampling frequency can be based on the total variation in a projection). The embodiment illustrated in FIG. 4 uses this consideration for the dynamic adjustment of the sampling frequency based on an analysis of the spatial frequency content of the considered "previous projection" $P_1$. This approach requires that the analysis of the projection data is fast enough to guide the acquisition based on recently acquired projection data.

In a helical stereo tube CT scanner such as the apparatus 100 of FIG. 1, one X-ray source is more advanced in the helical scan direction. The data obtained from this source can be analyzed dynamically during the scan to estimate an optimal subsampling rate for a given z-range in the patient and a given projection angle. The sub-sampling frequency for this z-range of the other source can be adjusted dynamically according to this optimum.

Figure 5:
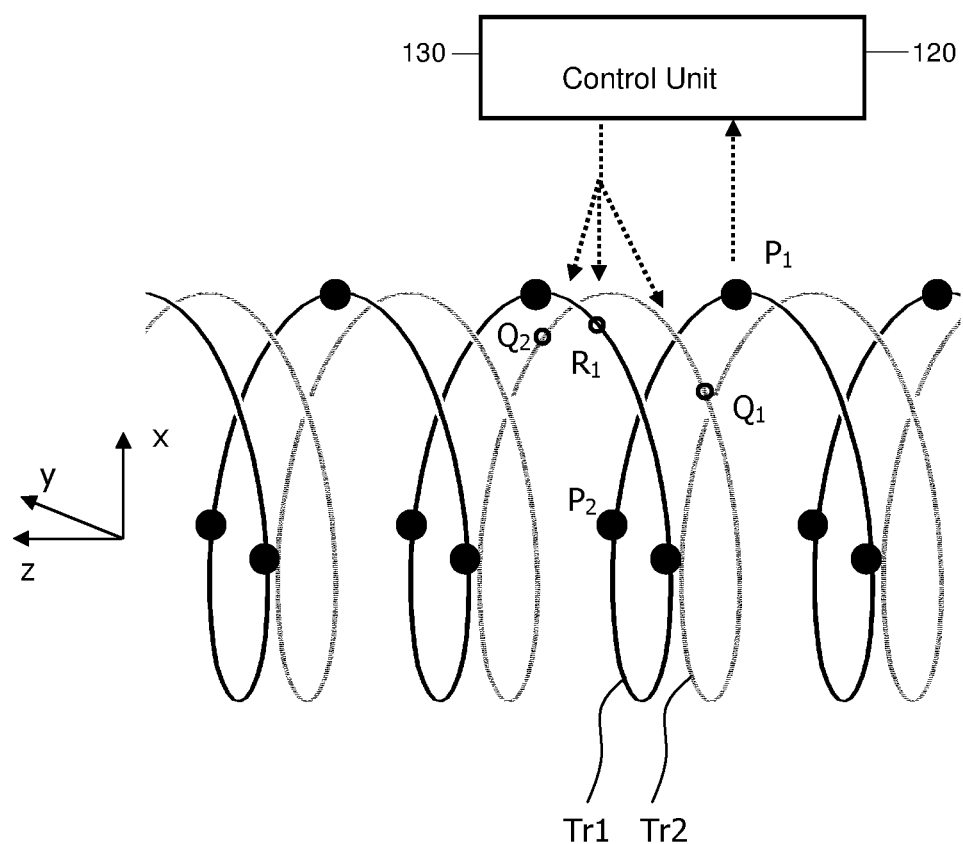
FIG. 5 shows a schematic perspective view of the helical scanning path of a first X-ray source and the helical scanning path of an additional X-ray source when additional projections are dynamically introduced in both paths.

FIG. 5 illustrates the aforementioned embodiment. The first X-ray source 111 advances along a first helical path Tr1, generating first projections $P_1$, $P_2$, . . . at equidistant angles according to a sparse angular sampling scheme. The additional X-ray source 112 advances along a second helical path Tr2, and additional projections $Q_1$, $Q_2$ may be generated by activation of this additional X-ray source. Optionally further additional projections $R_1$, . . . may be generated by supplementary activations of the first X-ray source 111 along the first helical path Tr1, too.

Some of the generated projections may be taken as "previous projections" which are evaluated for a dynamic decision of additional projections have to be inserted. In the shown example, one first projection $P_1$ has been taken as "previous projection", and it has been decided to introduce two additional projections $Q_1$, $Q_2$ on the second scan path Tr2 and one additional projection $R_1$ on the first scan path Tr1.

In summary, embodiments have been described that relate to a CT imaging apparatus and a method for generating sectional images of an object such as a patient on a patient table. According to one embodiment, first projections are generated along a first helical scanning path of a first X-ray source according to a sparse angular sampling scheme. Additional projections may dynamically be introduced along said first helical scanning path and/or along a second helical scanning path of an additional X-ray source based on the evaluation of previous projections.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A CT imaging apparatus for generating sectional images of an object, comprising:

at least one X-ray source for emitting an X-ray beam towards the object;

an X-ray detector for generating projections from the X-ray beam;

a control unit for controlling the activity of the X-ray source such that a) first projections are generated according to a sparse angular sampling scheme with less than about one projection per image voxel in one dimension;

b) additional projections are generated additionally to those of the sparse angular sampling scheme;

a reconstruction unit for reconstructing a sectional image of the object from the first projections and the additional projections.

2. The apparatus according to claim 1, characterized in that it comprises a first X-ray source and an additional X-ray source, wherein the additional X-ray source is controlled by the control unit to generate additional projections.

3. The apparatus according to claim 1, characterized in that an additional projection is generated in each angular interval between two first projections.

4. The apparatus according to claim 1, characterized in that first projections are generated at equidistant angular positions.

5. The apparatus according to claim 1, characterized in that at least one additional projection is dynamically introduced depending on the evaluation of at least one previous projection.

6. The apparatus according to claim 5, characterized in that the additional projection is introduced if the previous projection shows an increased content of higher spatial frequencies.

7. The apparatus according to claim 5, characterized in that the previous projection is generated with a different X-ray source than the associated introduced projection.

8. The apparatus according to claim 5, characterized in that the additional projection is introduced at a viewing perspective that corresponds to the viewing perspective of the associated previous projection.

9. The apparatus according to claim 1, characterized in that the first projections, the additional projections and/or the previous projections are generated along a helical scanning path.

10. The apparatus according to claim 1, characterized in that reconstruction of the sectional image is done by an iterative procedure.

11. A method for generating sectional images of an object, said method comprising the following steps:

generating first projections of the object according to a sparse angular sampling scheme with less than about one projection per image voxel in one dimension;

generating additional projections of the object additionally to those of the sparse angular sampling scheme;

reconstructing a sectional image of the object from the first projections and the additional projections.

12. A non-transitory computer readable storage medium encoded with computer readable instructions, which, when executed by a processor, cause the processor to:

generate first projections of the object according to a sparse angular sampling scheme with less than about one projection per image voxel in one dimension;

generate additional projections of the object additionally to those of the sparse angular sampling scheme;

reconstruct a sectional image of the object from the first projections and the additional projections.

13. The non-transitory computer readable storage medium according to claim 12, wherein a control unit is provided to control the additional projections.

14. The non-transitory computer readable storage medium according to claim 12, wherein the additional projections are generated in each angular interval between two first projections.

15. The non-transitory computer readable storage medium according to claim 12, wherein the first projections are generated at equidistant angular positions.

16. The non-transitory computer readable storage medium according to claim 12, wherein at least one additional projection is dynamically introduced depending on the evaluation of at least one previous projection.

17. The non-transitory computer readable storage medium according to claim 12, wherein the additional projections are introduced if the previous projection has an increased content of higher spatial frequencies.

18. The non-transitory computer readable storage medium according to claim 12, wherein the additional projections are introduced at a viewing perspective that corresponds to the viewing perspective of the associated previous projection.

19. The non-transitory computer readable storage medium according to claim 12, characterized in that the first projections or the additional projections are generated along a helical scanning path.

20. The non-transitory computer readable storage medium according to claim 12, wherein the reconstruction of the sectional image is done by an iterative procedure.

* * * * *